United States Patent [19]

Chaikof et al.

[11] Patent Number: 4,906,465

[45] Date of Patent: Mar. 6, 1990

[54] ANTITHROMBOGENIC DEVICES CONTAINING POLYSILOXANES

[75] Inventors: Elliot L. Chaikof, Newton; Cynthia Sung, Cambridge; Edward W. Merrill, Belmont, all of Mass.

[73] Assignee: Massachusetts Institute of Technology, Cambridge, Mass.

[21] Appl. No.: 168,673

[22] Filed: Mar. 16, 1988

Related U.S. Application Data

[63] Continuation-in-part of Ser. No. 110,006, Oct. 19, 1987.

[51] Int. Cl.[4] .................... A61K 31/74; C08G 77/04; A61M 35/00
[52] U.S. Cl. ........................................ 424/78; 528/29; 623/1
[58] Field of Search ...................... 623/1; 604/64, 66; 528/29; 424/78

[56] References Cited

U.S. PATENT DOCUMENTS

| | | | |
|---|---|---|---|
| 4,378,435 | 3/1983 | Takagi et al. | 623/1 |
| 4,625,010 | 11/1986 | Hahn et al. | 528/15 |
| 4,666,745 | 5/1987 | Hahn et al. | 427/393.4 |
| 4,675,361 | 6/1987 | Ward, Jr. | 525/92 |
| 4,684,709 | 8/1987 | Ona et al. | 528/15 |
| 4,686,137 | 8/1987 | Ward, Jr. | 428/290 |

OTHER PUBLICATIONS

Pekala et al., *Biomaterials* 7:372-378 (1986).
R. W. Pekala, "Synthesis and Characterization of Polyether/Polysiloxane Networks for Blood-Interfacing Applications".
S. Hosaka et al., *J. Appl. Polym. Sci.*, 23, 2089-2098 (1979).
R. W. Pekala et al., *J. Colloid & Interface Sci.*, 101, 120-128, (1984).
R. W. Pekala et al., *Biomaterials*, 7, 372-378 (1986).
A. S. Hoffman, "Polymers in Medicine and Surgery", (Plenum Press, New York, 1974), 33-44.
R. W. Pekala et al., *Biomaterials*, 7, 379-385 (1986).
B. Kanner et al., *Industrial and Engineering Chemistry Product Research and Development*, 6(2), 88-92 (1967).
R. Langer, *Chem. Eng. Commun.*, 6, 1-48 (1980).
S. Wisniewski et al., *J. Membr. Sci.*, 6, 299-308 (1980).
J. M. Anderson et al., *ACS Symposium Series*, 31, 167-179 (1976).
M. P. Embrey et al., *Brit. Med. J.*, 28, 901-902 (1980).
C. T. Reinhart et al., *J. Membr. Sci.*, 18, 227-239 (1984).
B. K. Davis, *Proc. Natl. Acad. Sci., USA*, 71, 3120-3123 (1974).
Y. W. Chien, *ACS Symposium Series*, 33, 53-71 (1976).
T. J. Roseman et al., *ACS Symposium Series*, 33, 33-52 (1976).
S. Yolles, "Polymers in Medicine and Surgery", R. L. Kronenthal et al., eds. (Plenum Press, New York 1975), 245-261.

*Primary Examiner*—John Kight
*Assistant Examiner*—Carlos Azpuru
*Attorney, Agent, or Firm*—Hamilton, Brook, Smith & Reynolds

[57] ABSTRACT

A crosslinked polymer network comprising the reaction product of a polyethylene oxide and a polyglycidoxypropylsiloxane is described. These materials demonstrate low in vivo platelet retention as well as a low thrombogenicity. As such, they can provide antithrombogenic properties to blood contacting devices such as catheters, artificial hearts, ventricular grafts and cardiovascular suture.

12 Claims, 1 Drawing Sheet

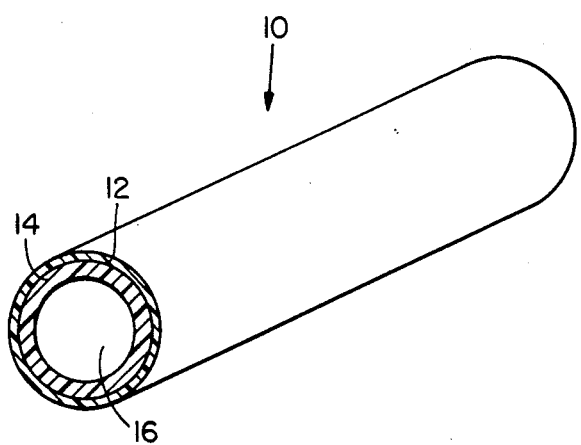

ANTITHROMBOGENIC DEVICES CONTAINING POLYSILOXANES

RELATED APPLICATIONS

This application is a continuation-in-part of U.S. Ser. No. 110,006, filed Oct. 19, 1987.

BACKGROUND OF THE INVENTION

The ability to repair, reconstruct and replace components of the cardiovascular systems of humans and animals is dependent upon the availability of blood compatible materials. Thromboresistant materials are also required for the development of long-term metabolic support and monitoring systems, as well as for the development of various blood diagnosis, treatment and storage systems.

A large number of polymeric materials have been suggested and evaluated as blood contacting materials. Unfortunately, a variety of biological events has often resulted in the failure of these materials as antithrombogenic surface layers.

Surface-induced thrombosis is the result of the interplay between surface characteristics and blood stream components. Protein adsorption, cellular adhesion and activation, and the initiation of coagulation and complement pathways are the basic phenomena which control the extent of thrombus formation and, therefore, the performance of a blood-contacting material.

While the sequence leading to surface-induced thrombus formation involves a number of complex interacting pathways, each is initiated by the adsorption of blood plasma proteins by the introduced surface. Thus, a key requirement for antithrombogenic materials is that they have a low degree of blood protein adsorption, thereby preventing the initiation of the thrombogenic pathways. To this end, it is known that most surfaces which are rough, crystalline or glassy, and hydrophobic have high degrees of protein binding. On the other hand, surfaces which are smooth, amorphous, solvated by water, and non-electrolytic may have, but do not necessarily have, low blood-protein adsorptivities.

Although a wide variety of materials are currently used in blood-contacting applications, the results are often less than satisfactory. For example, artificial heart technology has been hampered by the inability to prevent thrombus formation induced by the implant surfaces. This has resulted in severe cerebral-vascular damage in a number of artificial heart recipients.

Thus, a need exists for a blood-contacting material which can reduce thrombus formation, has good physical properties, and is non-toxic when implanted.

SUMMARY OF THE INVENTION

The invention pertains to the use as antithrombogenic materials of polymer networks which comprise the reaction product of a polyethylene oxide (PEO) and a glycidoxypropylsiloxane polymer (PGPS) and hydrogels thereof. These materials have been found to have excellent antithrombogenic properties. The antithrombogenic properties of these materials make them very suitable for applications in which blood contact is required, such as in biological implants. A further advantage of these materials is their biocompatibility. Several decades of clinical experience with silicone rubber implants have established that tissue reaction to these materials is very mild.

BRIEF DESCRIPTION OF THE DRAWINGS

The FIGURE is a schematic representation of an arterial graft having an inner, blood contacting surface which comprises the reaction product of a polyethylene oxide and a glycidoxypropylsiloxane polymer.

DETAILED DESCRIPTION OF THE INVENTION

This invention involves the synthesis and use of crosslinked polymer networks comprising the reaction product of a glycidoxypropylsiloxane polymer (PGPS) and a polyethylene oxide (PEO).

The PGPS materials described herein comprise chain polysiloxanes containing the structural units (A) and (B) as represented by Formula (1) below:

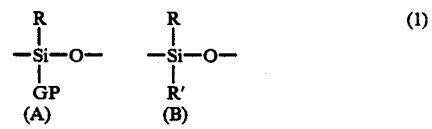

wherein GP is a glycidoxypropyl unit, and R and R' are —$CH_3$, —$C_2H_5$ or phenyl. Each PGPS molecule has between 3 and 25 (A) units, and the ratio of the number of (B) units to the number of (A) units is no greater than 10:1.

As used herein, the term polyethylene oxide (PEO) is defined to include the class of polymers characterized by repeat units of the form ($OCH_2CH_2$). One such compound is $\alpha,\omega$ dihydroxy PEO characterized by hydroxyl units at each terminal. In other PEO varieties, either one of the hydroxyl units can be replaced by a methyl group such as in polyethylene glycol monomethyl ether, or by an ethyl group such as in polyethylene glycol monoethyl ether. Alternatively, either or both of the hydroxyl groups can be replaced by an amino group such as in $\alpha,\omega$ diamino PEO. Other end capping groups for PEO are also known in the art.

The glycidoxypropyl (GP) units of this polymer are represented by Formula (2) below:

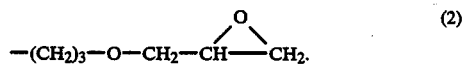

Representative siloxane polymers of this invention include polyglycidoxypropylmethylsiloxane, (PGPMS), and poly(glycidoxypropylmethylsiloxane/dimethylsiloxane), P(GPMS/DMS), copolymer. These materials are among those represented by general Formula (1) above and the abbreviation PGPS.

These siloxane polymers, existing as oily liquids similar to silicone oil, have been found to spontaneously emulsify water, whereas polydimethylsiloxane (PDMS) by itself does not. Additionally, when contacted with blood, networks of PEO and PGPS show a much lower platelet uptake than materials conventionally used for this purpose, thereby allowing these siloxane materials to be used as blood contacting surfaces for applications in which antithrombogenicity is desired. Such applications include artificial implants, arterial grafts and catheters.

When immersed in water, the reaction product of PEO and PGPS materials form a material known as a hydrogel. The term "hydrogel" refers to a broad class of polymeric materials which are swollen extensively in water but which do not dissolve in water. Hydrogels are described in greater detail in Hoffman, A. S., "Polymers in Medicine and Surgery", Plenum Press, N.Y., pp. 33-44 (1974), the teachings of which are incorporated herein by reference.

To form the crosslinked polymer networks of this invention, PEO is dissolved in an organic solvent for both PEO and PGPS. PEO-PGPS materials are synthesized by mixing PGPS into the PEO solution, followed by the dropwise addition of a ring-opening Lewis-acid catalyst such as dilute boron-trifluoride etherate. Other suitable catalysts include $BCl_3$, $AlCl_3$, $SbF_3$, $SbF_5$, $SbCl_5$. Exclusion of water is essential for the reaction of the PEO and PGPS to proceed properly. This may be accomplished by adding a drying agent such as molecular sieves, calcium hydride or calcium chloride to the solution, thereby removing trace amounts of water. The reacting solution is stirred and transferred to molds which are maintained under a saturated atmosphere of solvent for at least 8 hours. The polymer samples are then dried to effect the removal of the organic solvent.

Alternatively, a network can be formed by the reaction of a PGPS and $\alpha,\omega$ diamino PEO. In this case, the PGPS and the $\alpha,\omega$ diamino PEO are dissolved in an organic solvent. Rather than adding a catalyst, the reaction mixture is heated to increase the rate of reaction. The polymer network product is then dried to effect the removal of the organic solvent.

The synthesis of the preferred PGPMS materials is done by adding allyl glycidyl ether to polyhydromethylsiloxane (PHMS) via a catalyzed reaction. While catalysts such as rhodium and irridium may be used, platinum is preferred. Similarly, P(GPMS/DMS) is synthesized by starting with the PHMS/PDMS copolymer. A more detailed discussion of the synthesis of these preferred PGPMS compounds is described by Pekala, et al. (J. Colloid & Interface Sci. 101, 1984, pp. 120-128; and Biomaterials, 7, 1986, pp. 372-378) the teachings of which are hereby incorporated by reference.

A representative synthesis of this invention is given in Formula (3) below in which $\alpha,\omega$ dihydroxy PEO and a PGPS chain are contacted with boron trifluoride catalyst in a dichloromethane medium.

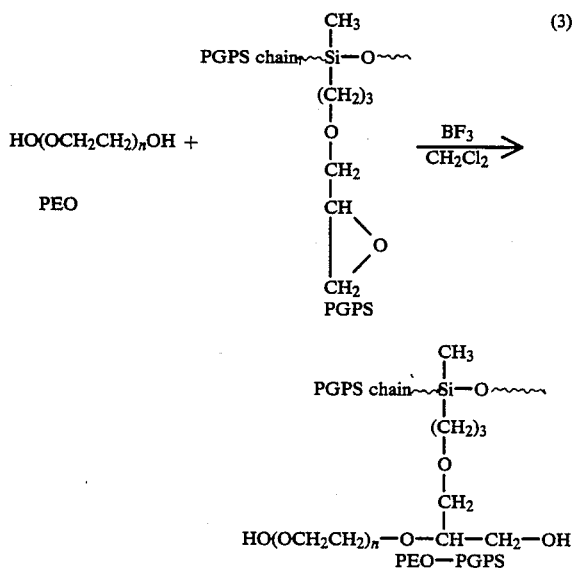

In Formula 3, n is between about 25 and about 500. In the preferred embodiment, n is greater than about 38. The mole ratio of glycidoxypropyl groups to hydroxyl groups in the initial mixture should be greater than 1:2 and preferably greater than 1:1. In a preferred embodiment, the mole ratio of glycidoxypropyl groups to hydroxyl groups is 3:2 or greater.

Emulsification properties of the PGPS precursor of the networks described herein can be illustrated in the following manner. An aliquot of water is gently layered upon the top of an aliquot of PGPS. Initially, two distinct and clear liquids are observed. Spontaneously, the interface between the polymer phase and the aqueous phase becomes progressively diffractive of light as a result of emulsification of water in polymer and vice versa. When an aliquot of water is mixed vigorously with an aliquot of liquid PGPS, three distinct phases form: the lowest phase being an emulsion of water in polymer, the middle phase being an emulsion of polymer in water, and the top phase being a clear aqueous solution. The emulsion is extremely stable and centrifugation at 9000 G for 30 minutes does not separate the polymer from water.

A variety of networks comprising PEO and PGPMS have been synthesized, cast onto fiberglass sleeves and evaluated in in vivo baboon studies for antithrombogenic properties. The results, as presented in the Examples section, indicate that such networks have a much lower thrombogenicity than expanded polytetrafluoroethylene, (e-PTFE), a widely used vascular graft material.

As such, networks of PEO and polysiloxanes can be used to cover surfaces of materials which contact blood for applications in which thrombus formation is undesirable. Such applications include use in cardiovascular devices such as vascular prostheses, artificial hearts, ventricular assist devices, intraaortic balloon pumps, pulmonary artery catheters, ventrical patches and cardiovascular suture. Another application for PEO/polysiloxane networks is in metabolic support systems such as long term intraarterial or intravenous catheters for monitoring, or administering medication or nutritional support. Additionally, these materials are not limited to in vivo use, being useful in ex vivo blood treatment, diagnosis or storage equipment. Such applications include use in devices such as hemodialysis membranes or membranes for extracorporeal oxygenators. Thus, these materials are intended to apply to any application involving blood contact in which it is desirable to avoid thrombus formation.

For example, one embodiment of a blood-contacting prosthesis as described by the present invention is set forth in the FIGURE. The FIGURE is a schematic representation of an arterial graft 10. The prosthesis has a generally tubular shape as defined by a cylindrical member 12. The cylindrical member 12 can be constructed of any of a variety of biocompatible material, however, polytetrafluoroethylene is preferred. The interior surfaces of the cylindrical member are covered with an antithrombogenic material 14 such as a crosslinked polymer network comprising the reaction product of a polyethylene oxide and a glycidoxypropylsiloxane having between 3 and 25 glycidoxypropyl units per molecule. In the preferred embodiment, the glycidoxypropylsiloxane comprises a poly(glycidoxypropylmethylsiloxane/dimethylsiloxane) copolymer. An axial pathway 16 contained within the prosthesis provides a channel through which blood can flow. In the preferred embodiment of arterial graft 10, every surface at which blood contact occurs comprises antithrombogenic material 14.

The invention is further and more specifically illustrated by the following examples.

EXAMPLE 1

Production of PEO-P (GPMS/DMS) Networks 20 g of PEO, nominal degree of polymerization of 45, was dissolved in 100 ml of dichloromethane. To remove trace water from this solution, 20 g of 3A molecular sieve was added to this solution and vigorously stirred for 12 hours under nitrogen. The solution was then filtered through a 0.5 micron filter. The final PEO concentration of this solution was measured by gel permeation chromatography (GPC) using differential refractometry detection. A similar procedure was carried out for P(GPMS/DMS), nominal degree of polymerization of 12:20 g of P(GPMS/DMS) was dissolved in 100 ml of dichloromethane. The solution was dried with 3A molecular sieves, stirred, filtered and analyzed by GPC under the same conditions as used with PEO described above.

A reaction between PEO and P(GPMS/DMS) was carried out under an atmosphere of nitrogen. A volume of PEO solution containing 0.5 g PEO and a volume of P(GPMS/DMS) solution containing 0.5 g P(GPMS/DMS) were mixed together, and a volume of dichloromethane was added so that the final total polymer concentration was 18.5%. An aliquot of boron trifluoride etherate was diluted 140 times in dichloromethane and 2 ml of this diluted catalyst was added dropwise and stirred into the polymer solution. Aliquots of solution were transferred into polyethylene molds and placed in a sealed container which contained a saturated atmosphere of dichloromethane. After 15 hours, the sample was removed and placed in a vacuum apparatus for complete removal of dichloromethane.

0.5 g of the resulting crosslinked PEO-P(GPMS/DMS) network was mixed with 20.0 ml of a 1.0 millimolar protriptyline solution in phosphate buffer (pH 7.4). After thorough stirring, the concentration of protriptyline in the remaining solution and in the initial solution was measured by liquid chromatography using a C18-silica column with ultraviolet detection at a wavelength of 254 nm. The partition coefficient K was calculated using Equation (2) (given previously) and found to be 224.

Example 2

Synthesis of Crosslinked Network Derived from Reaction of P(GPMS/DMS) and α,ω-diamino Polyethylene Oxide 0.5 g α,ω-diamino polyethylene oxide, nominal degree of polymerizaton of 45, and 0.5 g P(GPMS/DMS), nominal degree of polymerization of 12, were dissolved in 5 ml toluene. The solution was heated to 35° C. and maintained at that temperature in a closed container for fifteen hours. The crosslinked polymer was then transferred to a vacuum apparatus for complete removal of toluene.

It should be noted that this reaction can proceed in the absence of a catalyst, however, to obtain gelling in a short time (i.e., less than one day), the reaction mixture must be heated. The solvent toluene was substituted for dichloromethane, because toluene has a higher boiling point that dichloromethane, therefore making it easier to use at the elevated reaction temperature.

Example 3

In vivo Baboon Studies of PEO/PGPMS Networks

A stainless steel guidewire was covered with a 28 gauge fiberglass sleeve and then coated with a PEO/P(GPMS/DMS) network synthesized by the method described in Example 1. This polymer-coated guidewire was then passed up the cannulated femoral vein of a baboon. Blood capatibility was assessed by measuring $^{111}$In labeled platelet deposition following a one hour blood exposure period in the inferior vena cava. A total of nine different compositions, varying in PEO content from 0-65% and PEO nominal molecular weight from 2,000-20,000, were studied in triplicate. A sample of e-PTFE was also studied as a control. Following the removal of each test sample from the inferior vena cava, it was divided into multiple 1 cm segments.

Table A presents data for in vivo platelet uptake in terms of mean platelets retained per 1000 square microns of network material. In this table, the notation 2K, 8K and 20K means, respectively, PEO of molecular weight 2,000, 8,000 and 20,000; the notation 35, 50 and 65 refers to the percentage of the polymer network which comprises P(GPMS/DMS). The remainder of the network comprises PEO. The P(GPMS/DMS) entry refers to a network created without PEO. The control, e-PTFE, is expanded polytetrafluoroethylene.

Table A

| Material | Mean Platelet Retention/$1000\mu^2$ | Standard Error | No. of Segments Tested |
|---|---|---|---|
| PEO2K-35 | 5.62 | 1.12 | 20 |
| PEO2K-50 | 8.17 | 0.98 | 23 |
| PEO8K-35 | 5.30 | 1.87 | 17 |
| PEO8K-50 | 2.99 | 0.65 | 22 |
| PEO8K-65 | 5.36 | 0.94 | 19 |
| PEO20K-35 | 8.37 | 2.80 | 19 |
| PEO20K-50 | 2.31 | 0.43 | 21 |
| PEO20K-65 | 1.07 | 0.45 | 21 |
| P(GPMS/DMS) | 46.3 | 15.0 | 22 |
| e-PTFE | 7104.56 | 1061.5 | 21 |

The data presented in Table A show that the in vivo platelet retention for PEO/P(GPMS/DMS) is much lower than that of e-PTFE, a widely used vascular graft material, or P(GPMS/DMS) alone.

Equivalents

Those skilled in the art will know, or be able to ascertain using no more than routine experimentation, many equivalents to the specific embodiments expressly described herein. These are intended to be within the scope of the invention as described by the claims herein.

We claim:

1. A device for use with blood wherein all surfaces which contact blood comprise a crosslinked polymer network comprising the reaction product of a polyethylene oxide and a glycidoxypropylsiloxane having between 3 and 25 glycidoxypropyl units per molecule.

2. A device as in claim 1 wherein the glycidoxypropylsiloxane is a polyglycidoxypropylmethylsiloxane.

3. A device as in claim 1 wherein the glycidoxypropylsiloxane is a poly (glycidoxypropylmethylsiloxane/dimethylsiloxane) copolymer.

4. A device as in claim 1 wherein the polyethylene oxide is selected from the group consisting of dihydroxy polyethylene oxide, polyethylene glycol monomethyl ether, polyethylene glycol monoethyl ether, monoamino polyethylene oxide and diamino polyethylene oxide.

5. A device as in claim 1 wherein the polyethylene oxide has a molecular weight between about 2,000 and about 20,000.

6. A device as in claim 5 wherein the polyethylene oxide is selected from the group consisting of 2K PEO, 8K PEO and 20K PEO.

7. A device as in claim 1 wherein the crosslinked polymer network comprises between about 35% and about 65% polyethylene oxide by weight.

8. A device as in claim 1 wherein said device is selected from the group consisting of in vivo blood contacting vascular prostheses, artificial hearts, ventricular assist devices, intraaortic balloon pumps, pulmonary artery catheters, ventricular patches, cardiovascular suture and metabolic support catheters.

9. A device as in claim 1 wherein said device is selected from the group consisting of blood diagnosis apparatus, blood treatment apparatus and blood storage apparatus.

10. A device as in claim 9 wherein said device is selected from the group consisting of hemodialysis membranes and membranes for extracorporeal oxygenators.

11. In a device which contacts blood characterized by a need to prevent thrombus formation, the improvement which comprises providing all surfaces which contact blood with a covering comprising the reaction product of a polyethylene oxide and glycidoxypropylsiloxane having between 3 and 25 gylcidoxypropyl units per molecule.

12. A device for use with blood wherein all surfaces which contact blood comprise a cross-linked polymer network comprising the reaction product of a polyethylene oxide and a polyglycidoxypropylsiloxane having between about 3 and 25 glycidoxypropyl units per molecule.

* * * * *